(12) United States Patent
Jugl et al.

(10) Patent No.: US 9,849,246 B2
(45) Date of Patent: Dec. 26, 2017

(54) HOUSING OF A DRUG DELIVERY DEVICE

(71) Applicant: SANOFI-AVENTIS DEUTSCHLAND GMBH, Frankfurt am Main (DE)

(72) Inventors: Michael Jugl, Frankfurt am Main (DE); Axel Teucher, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 103 days.

(21) Appl. No.: 14/388,550

(22) PCT Filed: Mar. 20, 2013

(86) PCT No.: PCT/EP2013/055805
§ 371 (c)(1),
(2) Date: Sep. 26, 2014

(87) PCT Pub. No.: WO2013/143937
PCT Pub. Date: Oct. 3, 2013

(65) Prior Publication Data
US 2015/0073349 A1  Mar. 12, 2015

(30) Foreign Application Priority Data
Mar. 28, 2012  (EP) .................................. 12161665

(51) Int. Cl.
*A61M 5/24* (2006.01)
*A61M 5/315* (2006.01)

(52) U.S. Cl.
CPC .......... *A61M 5/24* (2013.01); *A61M 5/31525* (2013.01); *A61M 2005/2407* (2013.01)

(58) Field of Classification Search
CPC .......... A61M 5/24; A61M 5/178; A61M 5/20; A61M 5/31525; A61M 2005/2407;
(Continued)

(56) References Cited

U.S. PATENT DOCUMENTS 533,515 A  2/1895  Wilkens
5,226,895 A  7/1993  Harris
(Continued)

FOREIGN PATENT DOCUMENTS

DE  102009048497  3/2011
EP  0373321 B1  6/1994
(Continued)

OTHER PUBLICATIONS

European Search Report for EP Application No. 12161665.0, dated Jul. 27, 2012.
(Continued)

*Primary Examiner* — Bhisma Mehta
*Assistant Examiner* — Nilay Shah
(74) *Attorney, Agent, or Firm* — McDonnell Boehnen Hulbert & Berghoff LLP

(57) ABSTRACT

A housing for a drug delivery device is disclosed having a first housing component adapted to receive a cartridge at least partially filled with a medicament, and a second housing component adapted to receive a drive mechanism to operably engage with the cartridge for dispensing of a dose of the medicament, wherein the first housing component comprises an insert portion to be inserted in an axial direction into a corresponding receptacle of the second housing component, and wherein the insert portion comprises at least one radially outwardly extending first interlock member to positively engage and to rotationally lock with a correspondingly shaped second interlock member of the receptacle of the second housing component.

6 Claims, 2 Drawing Sheets

(58) Field of Classification Search
CPC .. A61M 2005/2433; A61M 2005/2437; A61M 2005/244; A61M 25/0625; A61M 2039/1033; A61M 2039/1094; B65D 17/06; A61J 1/1425; A61J 1/1481
See application file for complete search history.

(56) References Cited

U.S. PATENT DOCUMENTS

| | | | |
|---|---|---|---|
| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,835,187 | B2 | 12/2004 | Alexandre et al. |
| 6,899,698 | B2 | 5/2005 | Sams |
| 6,936,032 | B1 | 8/2005 | Bush, Jr. et al. |
| 7,241,278 | B2 | 7/2007 | Moller |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2006/0153693 | A1 | 7/2006 | Fiechter et al. |
| 2008/0097338 | A1* | 4/2008 | Cheng ............... A61M 5/24 604/201 |
| 2009/0254043 | A1* | 10/2009 | Van Bulow ........ A61M 5/24 604/207 |
| 2009/0275916 | A1 | 11/2009 | Harms et al. |
| 2011/0306940 | A1* | 12/2011 | Miyasaka ...... A61M 39/1011 604/256 |

FOREIGN PATENT DOCUMENTS

| | | |
|---|---|---|
| EP | 0937471 | 8/1999 |
| EP | 0937476 | 8/1999 |
| WO | 99/38554 | 8/1999 |
| WO | 00/35519 | 6/2000 |
| WO | 01/10484 | 2/2001 |
| WO | 2008/000827 | 1/2008 |
| WO | 2008/062025 | 5/2008 |
| WO | 2011/051365 A2 | 5/2011 |

OTHER PUBLICATIONS

International Search Report and Written Opinion for Int. App. No. PCT/EP2013/055805, dated Jun. 19, 2013.
International Search Report and Written Opinion for Int. App. No. PCT/EP2013/055805, completed Jun. 12, 2013.

* cited by examiner

HOUSING OF A DRUG DELIVERY DEVICE

CROSS REFERENCE TO RELATED APPLICATIONS

The present application is a U.S. National Phase Application pursuant to 35 U.S.C. §371 of International Application No. PCT/EP2013/055805 filed Mar. 20, 2013, which claims priority to European Patent Application No. 12161665.0 filed Mar. 28, 2012. The entire disclosure contents of these applications are herewith incorporated by reference into the present application.

TECHNICAL FIELD

The present invention relates to a housing of a drug delivery device and in particular to a housing of a pen-type injector to dispense a predefined amount of a liquid medicament.

BACKGROUND

Drug delivery devices allowing for multiple dosing of a required dosage of a liquid medicament, such as liquid drugs, and further providing administration of the medicament to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicament to be administered is provided in a cartridge that has a moveable piston or bung mechanically interacting with a piston rod of a drive mechanism of the drug delivery device. By applying thrust to the piston in a distal direction, a predefined amount of the medicinal fluid is expelled from the cartridge.

Especially with disposable drug delivery devices and pen-type injectors, the various components and parts the drug delivery device is made of typically comprise injection moulded plastic components. Also the housing of such drug delivery devices comprises various housing components of thermoplastic material. Most typically, drug delivery devices of pen-injector type typically comprise a distal housing component that serves as a cartridge holder and further comprise a proximal housing component to engage with the distal housing component and being further adapted to accommodate a drive mechanism to operably engage with the cartridge for dispensing a predefined amount of the medicament provided therein.

When the housing components are manufactured as injection moulded plastic parts, which, by virtue of appropriately selected thermoplastic materials feature a particular elasticity, such components can support a snap-fitting and an inseparable positively engaged interconnection.

However, since such drug delivery devices are predominately intended for home medication, the device has to fulfil highest possible standards in terms of failure safety and robustness, especially in view of mechanical impact.

Moreover, the mutual interconnection of the distal and proximal housing components has to be rather rigid and free of tolerances in order to immediately provide a counter force when a dose dispensing action is initiated, during which the drive mechanism of the drug delivery device exerts distally directed thrust or pressure towards the piston of the cartridge.

If for instance such a device drops down from a considerably height, a mechanical load-distribution may rise above a critical level in the interconnection of cartridge holder and body. Such point stresses or point loading may well exceed a critical level and as a consequence the interconnection of cartridge holder and body may break down such that device would be no longer of use.

One possible object of the present invention is to provide a mechanically stable, reliable, cost-efficient and precisely fitting housing for a drug delivery device in particular for a pen-type injector.

SUMMARY

In a first aspect, the invention provides a housing for a drug delivery device and in particular a housing for a pen-type injector. The housing comprises a first housing component or distal housing component adapted to receive a cartridge being at least partially filled with a medicament to be dispensed by means of the drug delivery device. The housing further comprises a second housing component which is adapted to receive or to accommodate a drive mechanism. The drive mechanism is to be operably engaged with the cartridge to dispense a dose of the medicament.

First and second housing components mutually engage in a common interface section, in which first and/or second housing components comprise a receptacle and a corresponding insert portion. In particular, the first housing component comprises an insert portion to be inserted into a correspondingly shaped receptacle of the second housing component. Mutual and partial intersection of first and second housing components occurs in an axial direction, hence substantially parallel to the distal and/or proximal elongation of the drug delivery device.

It is of particular benefit when the first housing component comprises the insert portion at its proximal end. This way, it can be inserted into the corresponding receptacle provided at a distal end of the second housing component.

Furthermore, the insert portion of the first housing component comprises at least one, preferably several radially outwardly extending first interlock members to mate and/or to engage with a second interlock member of the receptacle of the second housing component. First and second interlock members of first and/or second housing components mutually match and mutually engage when first and second housing components reach a final assembly configuration.

Moreover, the first and the second housing components are directly interconnectable with each other by way of a positive and rotational interlocking of first and second interlock members. This way, first and second housing components can be axially and circumferentially, hence rotationally fixed with respect to each other.

The positive engagement of first and second housing components is of two- or three-dimensional type which preferably inhibits any kind of relative displacement between first and second housing components once said housing components are mutually engaged or interlocked.

By way of the positive engagement, the manufacturing and assembly process of first and second housing components is rather easy and intuitive. For instance, first and second housing component can be mutually assembled by way of a snap-fit or clip-like interconnection.

It is of particular benefit and according to a preferred embodiment when first and second housing components at least partially comprise a substantially tubular or cylindrical geometry. Mutual insertion of first and second housing components take place in axial direction whereas the positive and/or rotational engagement or interlock of first and second housing components is provided in radial and/or tangential direction.

In a preferred embodiment, the first interlock member comprises at least one radially extending lug to engage with a correspondingly shaped radially extending recess at an inside facing side wall portion of the receptacle. Here, the radially extending recess serves as the second interlock member. Alternatively, also the second interlock member may comprise at least one radially extending lug to engage with a radially extending recess at an outside facing side wall portion of the insert portion.

It is of particular benefit when the interface comprised of insert portion and receptacle comprises a plurality of mutually corresponding pairs of interlock members, distributed along the outer circumference of the insert portion and along the inner circumference of the receptacle. This way mechanical point loads can be minimized and mechanical stress that may arise across the interface between first and second housing components can be effectively reduced.

The at least one recess may comprise a somewhat concave shaped indentation in the inside facing side wall of the recess. Hence, the recesses do not intersect the side wall of the receptacle and can therefore provide a rather closed structure, which is beneficial in terms of the overall stability and rigidity of the housing.

Furthermore and according to another embodiment, the second interlock member comprises a circumferential and/or annular groove. The groove may be provided as a radially outwardly extending recess at an inside facing side wall portion of the receptacle of the second housing component.

However, it is also conceivable and according to an alternative embodiment, that the first interlock member provided at the insert portion of either first or second housing component comprises a circumferential groove, preferably extending radially inwardly to engage with a correspondingly shaped radially inwardly extending second interlock member featuring at least one radially inwardly extending lug.

In a further preferred embodiment, the circumferential groove comprises an undulated structure. Consequently, the groove comprises several groove portions located at different axial positions with regard to the overall tubular geometry of first or second housing components. By way of such an undulated structure a rotational interlock can be provided when the second interlock member comprises correspondingly shaped and/or correspondingly positioned radially extending lugs located axially offset to engage with respective groove portions of the second interlock member.

In a further preferred aspect, also the first interlock member comprises a radially outwardly extending rim to mate with the circumferential groove of the second interlock member. The rim as well as the groove might be interrupted in circumferential, hence tangential direction, in order to break or to interrupt a rotational symmetry of the interface between first and second housing components. Consequently, the rim and/or the corresponding groove may comprise several separated rim- and groove portions.

However, the rim may also comprise a substantially undulated structure to fit into the undulated structure of the groove. Furthermore, the rim may also extend completely around the insert portion to form a circumferentially closed structure.

By means of mutually correspondingly shaped grooves and rims, a rotational and axial interlock of first and second housing components can be provided with an increased contact- or engagement surface. In this way point loads between first and second housing components and between their mutually engaging interlock members can be substantially reduced.

The undulations of the groove preferably extend in axial direction while the groove itself substantially extends in a plane perpendicular to the overall elongation of the housing and/or cartridge holder. The undulated structure of the groove, hence the undulations of the groove may be periodically shaped and may comprises a regular, e.g. sinusoidal and/or wave-like shape. When travelling along the groove in circumferential or tangential direction the groove and its undulations may regularly vary in axial direction. Typically the groove comprises at least two or even more periods of undulations.

Apart from regular and/or periodically shaped undulations it is also conceivable that the annular or circumferentially extending groove of the receptacle comprises a rather irregular shape that corresponds with the shape and/or position and/or orientation of the first housing component's interlock member.

In a further preferred embodiment, the interface section of first and second housing components comprises at least two mutually engaging first and second interlock members being regularly or irregularly arranged along the circumference of the interface section. When providing numerous regularly or equidistantly arranged interlock members at the interface of first and second housing components, said housing components can be interconnected and/or interlocked in at least two different orientations. However, if the interlock members are irregularly arranged on the circumference of the interface section, only a few or a single mutual orientation of first and second housing components may be suitable to attain a mutual interconnection and rotational interlocking thereof.

In still another aspect, the first housing component comprises a cartridge holder to receive and to accommodate a cartridge at least partially filled with the medicament. Preferably, the cartridge is to be pre-assembled in the first housing component prior to a mutual assembly of first and second housing components. Likewise, also the drive mechanism is to be preassembled in the second housing component to provide a drive mechanism preassembly in a final step of assembly, in which the cartridge holder preassembly and the drive mechanism preassembly are to be mutually interconnected, simply by a positive interlock of first and second housing components.

When designed as a disposable device it is of further benefit, when the interlock of first and second housing components is of inseparable or inextricable or non-detachable type. Hence, once the interconnection of first and second housing components has been established, it cannot be released without destroying one of first or second housing components. This way, the housing provides an effective protection against unintended repeated use of the drug delivery device once the medicament provided in the cartridge has been used up or consumed.

In a further independent aspect, the invention also provides a drug delivery device for dispensing a pre-defined amount of a medicament. The drug delivery device comprises a cartridge at least partially filed with a medicament and a drive mechanism to operably engage with the cartridge in order to dispense a pre-defined amount of the medicament. Furthermore, the drug delivery device comprises a housing as described above, wherein the cartridge is accommodated in the first housing component that serves as a cartridge holder and wherein the drive mechanism is arranged in the second housing component.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)$_{25}$, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)$_5$des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the drawings, in which.

DETAILED DESCRIPTION

Figure 1:
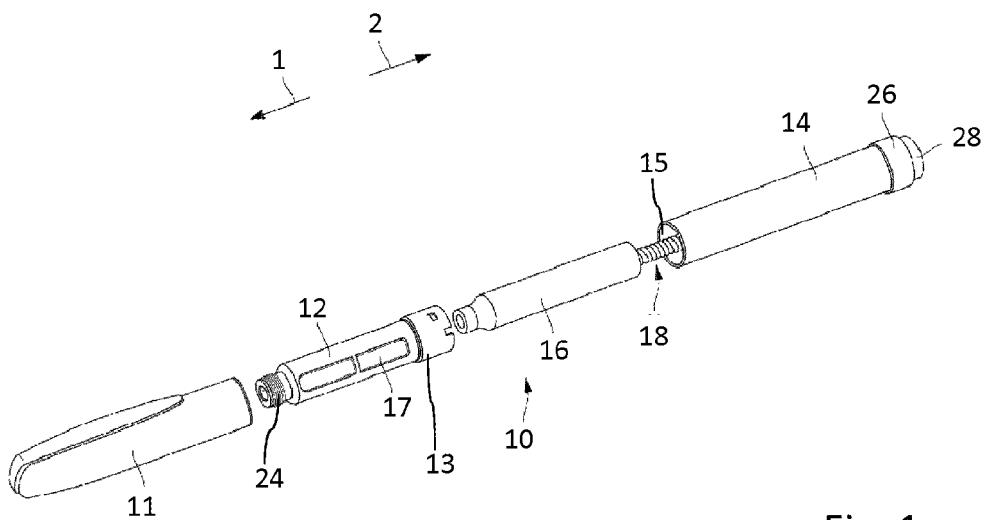
FIG. 1 schematically illustrates an exploded perspective view of a drug delivery device of pen-injector type.

The drug delivery device 10 as depicted in FIG. 1 comprises at least two housing components, a first housing component 12 serving as a cartridge holder to receive a cartridge 10 and a second or proximal housing component 14 that serves as a body of the drug delivery device 10 and which is adapted to receive and to accommodate a drive mechanism 18 which is intended to operably engage with a piston of the cartridge 16 in order to exert distally directed pressure thereon. The body or main housing component 14 is further equipped with a dose dial 26 and with a dose button 28 by way of which a dose of the medicament can be set and subsequently dispensed.

The first and distal housing component 12 further comprises a threaded socket 24 at its distal end in order to receive a correspondingly threaded needle hub having a double-tipped needle which is adapted to penetrate a distally located septum of the cartridge 16 to get access to the inner volume of the cartridge 16 and to the medicament. The opposite tipped end of such a needle is adapted to puncture biological tissue in order to deposit and to inject the medicament therein. Additionally, the cartridge holder 12 comprises an inspection window 17 to visually inspect a filling level of the cartridge 16 disposed therein. If not in use, the cartridge holder 12 can be protected by a removable cap 11.

Figure 2:
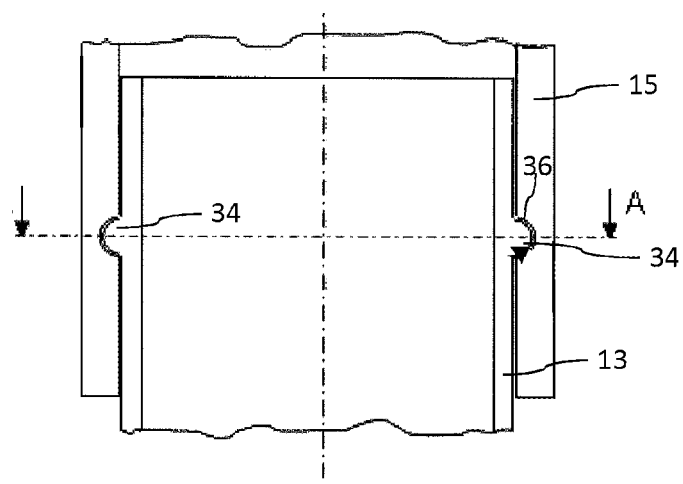
FIG. 2 shows a longitudinal cross section of the interface between first and second housing components.

As can be further seen from the sketch of FIG. 1, the first housing component or cartridge holder 12 comprises an insert portion 13 at its proximal end by way of which the cartridge holder 12 can be at least partially inserted in a correspondingly shaped receptacle portion 15 at a distal end of the second housing component 14. As further illustrated in the cross section of FIG. 2, the insert portion 13 of the cartridge holder 12 comprises numerous radially outwardly extending lugs 34 that positively engage with correspondingly shaped recesses 36 provided at the inside facing side wall of the receptacle portion 15 of the body 14.

This way, a three-dimensional positive and rotational interlock of first and second housing components 12, 14 can be established allowing to assemble first and second housing components 12, 14 in an easy and intuitive as well as inseparable way.

Here, it is of particular benefit, that the recess 36 is not designed as a circumferential groove, which would otherwise enable a mutual twisting of first and second housing components 12, 14 when assembled.

Figure 3:
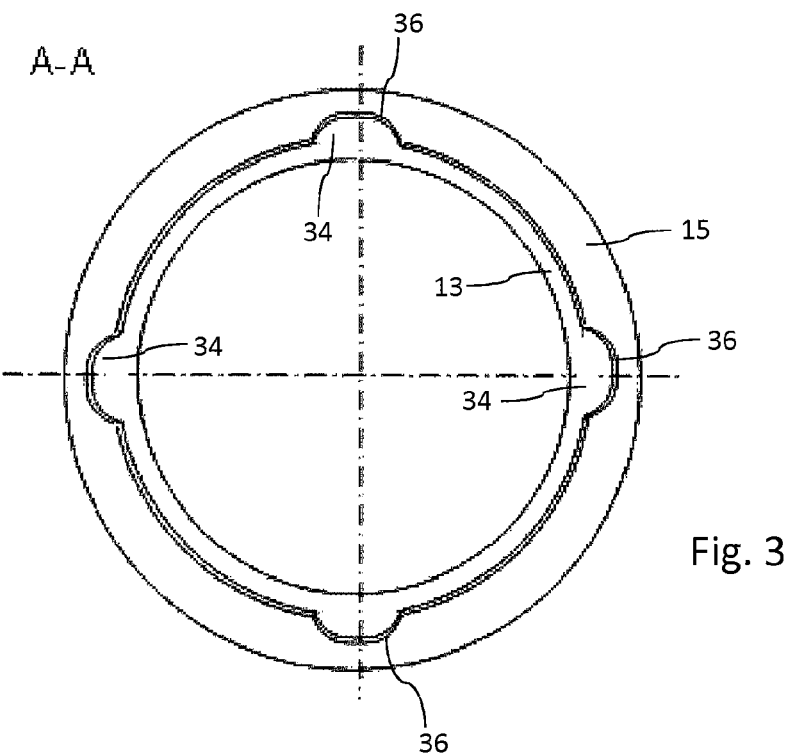
FIG. 3 shows a cross-section along A-A according to FIG. 2, and FIG. 4 schematically illustrates an undulated groove as an interlock member.

As seen in FIG. 3, there are provided four equidistantly arranged pairs of lugs 34 and recesses 36, by way of which mechanical forces acting on the interface 30 of first and second housing components 12, 14 can be circumferentially distributed, compensated and/or absorbed.

Figure 4:
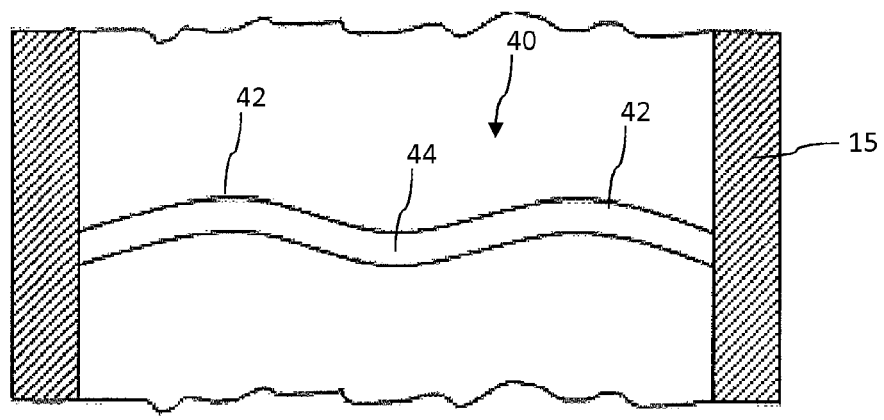

FIG. 4 finally illustrates an alternative embodiment, wherein the receptacle portion 15 of the second housing component 14 comprises a circumferentially and radially outwardly extending groove 40 at the inside facing side wall of the receptacle portion 15. The groove 40 comprises an undulated structure featuring groove portions 42, 44 that are arranged axially offset. Hence, the axial position in either distal direction 1 or proximal direction 2 of a groove portion 42 differs from an adjacent groove portion 44.

Said undulated groove 40 of e.g. wave form characteristic may be designed to receive numerous radially outwardly extending lugs 34 as shown in FIG. 3, which may be arranged axially offset accordingly. For instance a first lug 34 may engage with a groove portion 42 while another, axially offset lug 34 may engage with a groove portion 44 with a corresponding axial offset. Such mutual interconnection or interlocking may also prevent a relative rotation of first and second housing components 12, 14.

It is of further benefit when the insert portion 15 comprises a radially outwardly extending rim that matches with the geometry and slope of the groove 40. This way an annular and circumferential abutment of rim and groove can be attained. Mechanical loads transmitted via the interface between first and second housing components 12, 14 can be circumferentially and more evenly distributed so that punctual stress and punctual mechanical load across the interface of first and second housing components 12, 14 can be effectively reduced.

This way the housing can be effectively stabilized against external impact and becomes less prone to fracture or rupture, e.g. when dropped to the ground.

The invention claimed is:

1. A housing for a drug delivery device, comprising:
a first housing component adapted to receive a cartridge at least partially filled with a medicament,
a second housing component adapted to receive a drive mechanism to operably engage with the cartridge for dispensing of a dose of the medicament,
wherein the first housing component comprises an insert portion to be inserted in an axial direction into a corresponding receptacle of the second housing component, and
wherein the insert portion comprises at least one radially outwardly extending first interlock member to positively engage and to lock with a correspondingly shaped second interlock member of the receptacle to rotationally fix the first and the second housing components with respect to each other characterized in that,
the first and the second housing components are mutually assembled by a snap-fit interconnection, wherein an interlock of the first and the second housing components is of inseparable or non-detachable type, and wherein
the second interlock member comprises a circumferentially extending groove comprising a wave-like undulated structure and having at least a first groove portion and a second groove portion circumferentially adjoining the first groove portion and wherein the first and the second groove portions are arranged axially offset from each other and wherein the first interlock member comprises at least one radially extending lug to engage with the groove.

2. The housing according to claim 1, wherein the first and the second housing components comprise a substantially tubular geometry.

3. The housing according to claim 1, further comprising at least two first interlock members being regularly or irregularly arranged at the circumference of the insert portion.

4. The housing according to claim 1, wherein the first housing component comprises a cartridge holder having the cartridge disposed therein.

5. The drug delivery device for dispensing a pre-defined amount of the medicament, comprising:

the housing according to claim 1, the cartridge at least partially filled with the medicament, and the drive mechanism to operably engage with the cartridge.

6. The housing according to claim 1, wherein the circumferentially extending groove comprises a third groove portion circumferentially adjoining the second groove portion at a side facing away from the first groove portion and wherein the first and the third groove portions are arranged at the same or overlapping axial positions.

* * * * *